US012661062B2

(12) United States Patent
Ohayon

(10) Patent No.: US 12,661,062 B2
(45) Date of Patent: Jun. 23, 2026

(54) APPLICATION BASED DETERMINATION OF A DEGREE OF INEBRIATION

(71) Applicant: BRIGHTERMD LLC, Plano, TX (US)

(72) Inventor: Jesse Ohayon, Plano, TX (US)

( * ) Notice: Subject to any disclaimer, the term of this patent is extended or adjusted under 35 U.S.C. 154(b) by 308 days.

(21) Appl. No.: 18/471,244

(22) Filed: Sep. 20, 2023

(65) Prior Publication Data

US 2025/0090091 A1 Mar. 20, 2025

(51) Int. Cl.
| | |
|---|---|
| *A61B 5/00* | (2006.01) |
| *A61B 5/145* | (2006.01) |
| *A61B 5/1455* | (2006.01) |
| *A61B 5/16* | (2006.01) |
| *A61B 5/18* | (2006.01) |
| *G06Q 10/105* | (2023.01) |
| *G06T 7/00* | (2017.01) |
| *G06T 7/90* | (2017.01) |

(52) U.S. Cl.
CPC ........ *A61B 5/4845* (2013.01); *A61B 5/14546* (2013.01); *A61B 5/1455* (2013.01); *A61B 5/163* (2017.08); *A61B 5/18* (2013.01); *A61B 5/6898* (2013.01); *A61B 5/7267* (2013.01); *A61B 5/746* (2013.01); *G06Q 10/105* (2013.01); *G06T 7/0012* (2013.01); *G06T 7/90* (2017.01); *A61B 2503/20* (2013.01); *G06T 2207/20081* (2013.01); *G06T 2207/20084* (2013.01); *G06T 2207/30201* (2013.01)

(58) Field of Classification Search
CPC ... A61B 5/4845; A61B 5/163; A61B 5/14546; A61B 5/1455; A61B 5/18; A61B 5/6898; G06T 7/90
See application file for complete search history.

(56) References Cited

U.S. PATENT DOCUMENTS

| | | | |
|---|---|---|---|
| 8,684,922 B2 | 4/2014 | Tran | |
| 10,610,111 B1 | 4/2020 | Tran | |
| 10,694,988 B2 | 6/2020 | Lee et al. | |
| 11,096,581 B2 | 8/2021 | Hickle et al. | |
| 11,204,281 B1 * | 12/2021 | Ouellette | G06V 40/166 |
| 11,308,618 B2 | 4/2022 | Connor | |
| 11,342,076 B1 | 5/2022 | Jagirdar et al. | |
| 11,430,098 B2 * | 8/2022 | Harrison | G06N 3/08 |
| 11,501,510 B2 * | 11/2022 | Chiu | G06V 40/10 |

(Continued)

FOREIGN PATENT DOCUMENTS

| | | |
|---|---|---|
| GB | 2586433 A | 2/2021 |
| KR | 1020220019340 A | 2/2022 |
| WO | 2021055427 A1 | 3/2021 |

*Primary Examiner* — Mohammed H Zuberi
(74) *Attorney, Agent, or Firm* — Scheef & Stone, L.L.P.; Keith C. Rawlins, Esq.

(57) ABSTRACT

A method, application program, smart device, and computer system may capture images of a face of a user, determine one or more vital signs of the user by image processing optionally assisted by a machine learning model, determine a physiological state for one or more of the vital signs with a computational model generated by another machine learning model, determine a pupil-to-iris pixel ratio for an eye of the user in at least one of the plurality of images, and determine a degree of inebriation of the user based on i) the pupil-to-iris pixel ratio and ii) the physiological state for the vital sign, the value for the vital sign, or both the physiological state for the vital sign and the value for the vital sign.

20 Claims, 5 Drawing Sheets

(56)  References Cited

U.S. PATENT DOCUMENTS

| | | | |
|---|---|---|---|
| 11,604,511 B2 * | 3/2023 | Tzvieli | G06F 3/013 |
| 11,627,204 B2 * | 4/2023 | Yamauchi | G06Q 30/02 |
| | | | 709/203 |
| 11,670,323 B2 * | 6/2023 | Kushwah | G10L 25/66 |
| | | | 382/100 |
| 11,798,317 B2 * | 10/2023 | Dabija | G06V 40/174 |
| 12,039,539 B2 * | 7/2024 | Kurylko | G06Q 20/322 |
| 12,093,457 B2 * | 9/2024 | Yildiz | G06F 3/015 |
| 12,399,363 B2 * | 8/2025 | Taylor | B60W 50/14 |
| 2006/0147094 A1 * | 7/2006 | Yoo | G06V 40/193 |
| | | | 382/117 |
| 2008/0166992 A1 | 7/2008 | Ricordi et al. | |
| 2009/0088607 A1 | 4/2009 | Muraca | |
| 2017/0011192 A1 | 1/2017 | Arshad et al. | |
| 2018/0300589 A1 * | 10/2018 | Levinshtein | G06F 3/012 |
| 2020/0029837 A1 | 1/2020 | Joudi | |
| 2020/0390337 A1 * | 12/2020 | Frank | A61B 5/0205 |
| 2021/0361208 A1 * | 11/2021 | Lee | G16H 50/20 |
| 2021/0407669 A1 | 12/2021 | Fish et al. | |
| 2022/0138941 A1 | 5/2022 | Yen et al. | |
| 2022/0142590 A1 | 5/2022 | Modai et al. | |
| 2022/0378319 A1 * | 12/2022 | Everman | G16H 40/63 |
| 2024/0273724 A1 * | 8/2024 | Koukiou | G01J 5/48 |
| 2024/0389854 A1 * | 11/2024 | Liao | A61B 5/0002 |

* cited by examiner

2000

CAPTURE IMAGES — 2100

DETERMINE HEMOGLOBIN CONCENTRATION (HC) CHANGES — 2200

DETERMINE BITPLANES THAT REPRESENT HC CHANGES — 2300

EXTRACT VALUE FOR VITAL SIGN FROM THE BITPLANES — 2400

BUILD FEATURE SET HAVING HC CHANGES — 2500

PERFORM TRAINED ML MODEL ON FEATURE SET TO OUTPUT PHYSIOLOGICAL STATE FOR VITAL SIGN — 2600

DETERMINE PUPIL-TO-IRIS PIXEL RATIO — 2700

DETERMINE DEGREE OF INEBRIATION — 2800

3000 ⟍

600

650

Iris Pixels: 24
Pupil Pixels: 7
P/I Pixel Ratio: 0.29 (29%)

Iris Pixels: 194
Pupil Pixels: 144
P/I Pixel Ratio: 0.74 (74%)

APPLICATION BASED DETERMINATION OF A DEGREE OF INEBRIATION

FIELD OF THE DISCLOSURE

The present disclosure generally relates to application based determination of a degree of inebriation of a user of the application.

BACKGROUND

Employee and contractor safety are often a concern for employers. Some jobs involve operation of equipment that requires focus and concentration. Employees and contractors are generally trained to perform their duties in a safe and accident-free manner in accordance with regulations and laws, and also free of substances such as alcohol, cocaine, methamphetamine, LSD, and THC. To enforce substance-free performance of duties, employers may have a drug testing program where employees or contractors are tested randomly and/or periodically for presence of any substance that is desired to be monitored. These tests do not monitor daily or hour-to-hour inebriation state of an employee or contractor.

Moreover, the availability of these substances through legal and illegal channels of trade gives rise to employee and contractor consumption of these substances during work hours, where the consumption can go undetected on a daily, hour-to-hour basis. For example, an employee such as a forklift operate can arrive at work sober and perform duties on a first shift (e.g., a morning shift). The employee can take a lunch break and consume alcoholic drinks that cause the employee to become inebriated. The employee may return to work inebriated and can cause damage to equipment and risk injury to themselves or others. In another example, vaping pipes are readily available in the marketplace and easily concealable, and employees or contractors can periodically vape while performing duties, sometimes performing duties in an inebriated state that goes undetected because the frequency of the drug testing program is too low to detect this type of inebriation.

Managers and supervisors, when present, can observe employees and contractors for inebriation, but the judgment of the human manager or supervisor regarding another's inebriation state can be somewhat subjective.

There is a need to objectively detect inebriation in the workplace at a frequency that is higher than current drug testing programs.

SUMMARY

Disclosed is a method including: capturing, by a camera of a smart device, a plurality of images of a face of a user; determining, by the smart device, a plurality of hemoglobin concentration (HC) changes based on the plurality of images; determining, by the smart device, a set of bitplanes of the plurality of images that represent the plurality of hemoglobin concentration (HC) changes of the user; extracting, by the smart device, a value for a vital sign from the plurality of HC changes; building, by the smart device, a feature set including the plurality of HC changes; performing, by the smart device, a trained machine learning model including a computational model on the feature set to obtain an output data set including a physiological state for the vital sign; determining, by the smart device, a pupil-to-iris pixel ratio for an eye of the user in at least one of the plurality of images; and determining, by the smart device, a degree of inebriation of the user based on i) the pupil-to-iris pixel ratio and ii) the physiological state for the vital sign, the value for the vital sign, or both the physiological state for the vital sign and the value for the vital sign.

Disclosed is a computer system including a smart device, wherein the smart device is configured to: capture, by camera of the smart device, a plurality of images of a face of a user; determine, by an application program running on the smart device, a plurality of hemoglobin concentration (HC) changes based on the plurality of images; determine, by the application program, a set of bitplanes of the plurality of images that represent the plurality of hemoglobin concentration (HC) changes of the user; extract, by the application program, a value for a vital sign from the plurality of HC changes; build, by the application program, a feature set including the plurality of HC changes; perform, by the application program, a trained machine learning model including a computational model on the feature set to obtain an output data set including a physiological state for the vital sign; determine, by the application program, a pupil-to-iris pixel ratio for an eye of the user in at least one of the plurality of images; and determine, by the application program, a degree of inebriation of the user based on i) the pupil-to-iris pixel ratio and ii) the physiological state for the vital sign, the value for the vital sign, or both the physiological state for the vital sign and the value for the vital sign.

Other technical features may be readily apparent to one skilled in the art from the following figures, descriptions and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
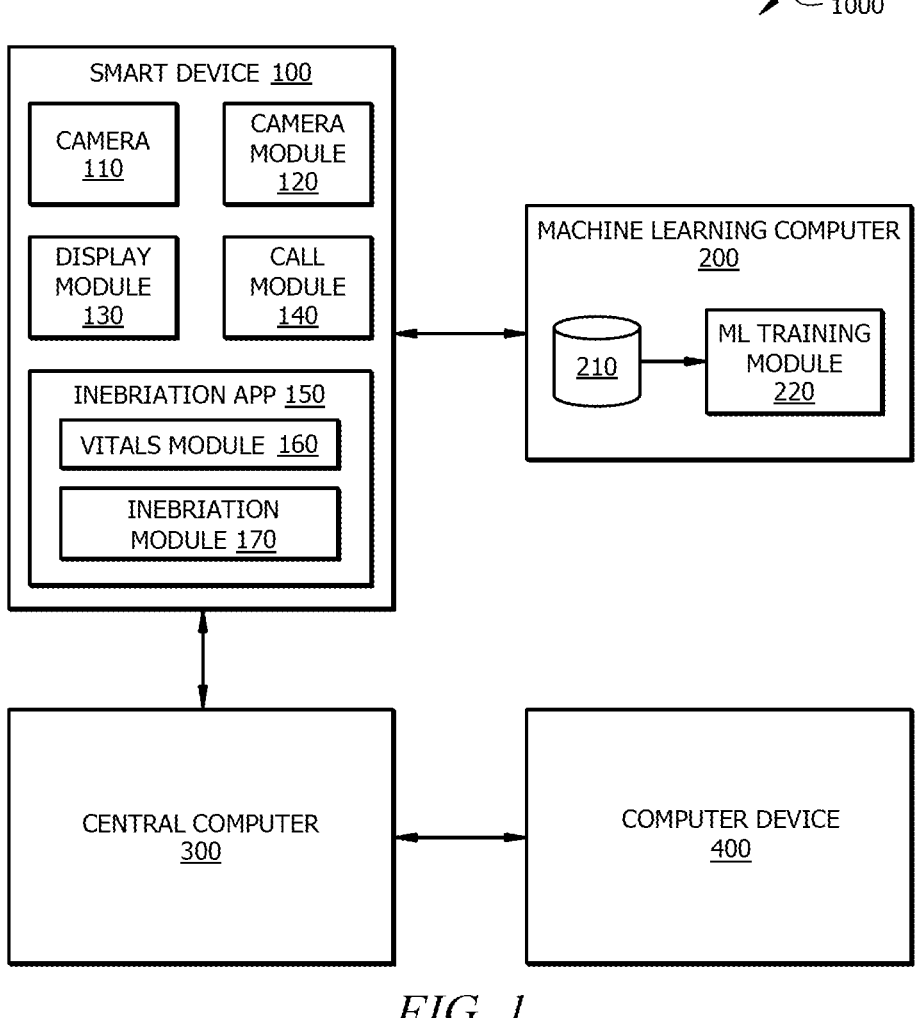
FIG. 1 illustrates a schematic diagram of a computer system for determining one or more vital signs of a user and a physiological state of a user with a smart device and for initiating an action in response to the determined physiological state.

"Application program" or "application" or "app" as used herein refers to instructions stored on and/or running on a user computer device, which when executed by a processor of the user computer device, cause the user computer device to perform the function(s) of the application disclosed herein.

"Vital sign" or "vital signs" as used herein can include, but are not limited to, heart rate, respiratory rate, blood pressure, blood oxygen index, temperature, or combinations thereof, of a user.

"Physiological state" as used herein refers to a status of a vital sign or combination of vital signs. For example, a physiological state of a user's vital sign that is determined by a technique disclosed herein can be normal, elevated, or severe. Additionally or alternatively, the physiological state of the user's vital sign that is determined by a technique disclosed herein can be relative to a risk of a medical event, e.g., low risk, normal risk, high risk relative to having a heart attack.

"Inebriation" as used herein refers to the physiological effect on a human body due to consumption of a substance, including but not limited to alcohol, cocaine, methamphetamine, lysergic acid diethylamide (LSD), and tetrahydrocannabinol (THC).

Disclosed herein are methods, application program, smart device, and computer system that may capture images of a face of a user, determine one or more vital signs of the user by image processing optionally assisted by a machine learning model, determine a physiological state for one or more of the vital signs with a computational model generated by another machine learning model, determine a pupil-to-iris pixel ratio for an eye of the user in the images; and determine a degree of inebriation based on i) the pupil-to-iris pixel ratio and ii) the physiological state, the value for the vital sign, or both the physiological state and the value for the vital sign.

In aspects, the methods, application program, smart device, and computer system can determine one or more vital signs of a user, a physiological state of the user, and a degree of inebriation of the user. The physiological state can be determined by a smart device running an application program disclosed herein because 1) images of a face of a user can be captured by the camera of the smart device, 2) the images can contain the color signature of hemoglobin concentration (HC), 3) the smart device can be programed to isolate HC changes from the images captured by the camera the smart device, and 4) the HC changes can be correlated to human physiological states. Particularly, a camera of a smart device can capture the re-emission of light from the skin of a user's face using the camera of the smart device. That is, light from a light source can enter the epidermis layer of the skin of the user and deflect or reflect from the epidermis and/or one or more layer of skin below the epidermis (e.g., papillary dermis or reticular dermis). The images captured by the camera of the smart device can contain the color signature of hemoglobin concentration in the deflected or reflected light.

FIG. 1 illustrates a schematic diagram of a computer system 1000 for determining one or more vital signs of a user and a physiological state of a user with a smart device 100 and for initiating an action in response to the determined physiological state. The computer system 1000 can include the smart device 100 (a smart device of a user), a machine learning computer 200, a central computer 300, and a computer device 400 (a smart device of an employer). While one user smart device 100 is illustrated in FIG. 1 as being networked with the machine learning computer 200 and the central computer 300, the disclosure contemplates that a plurality of user smart devices can be networked with the machine learning computer 200 and with the central computer 300, where each of the user smart devices contains the hardware and software functionality described for smart device 100 herein. Similarly, while one employer computer device 400 is illustrated in FIG. 1 as being networked with the central computer 300, the disclosure contemplates that a plurality of employer smart devices can be networked with the central computer 300, where each of the smart devices contains the hardware and software functionality described for computer device 400 herein.

The smart device 100 can be embodied as a smart phone, tablet, laptop, PC, or other computer device. Commercially available smart devices include Apple, Samsung, Google, and Huawei. The smart device 100 can have a camera 110, a camera module 120, a display module 130, a call module 140, and one or more application programs that include the application program 150 of this disclosure. In aspects, the smart device 100 can include chipsets that have a dedicated machine learning interference chip, such as those offered by Samsung, Qualcomm, ARM, Nvidia, or Huawei.

The application program 150 can have a vitals module 160 that is configured to determine one or more vital signs of a user and a physiological state of a user of the smart device 100 and an inebriation module 170 that is configured to determine a degree of inebriation of the user, as described in more detail herein.

The vitals module 160 of the application program 150 of the smart device 100 is configured to receive a first trained computational model from the machine learning computer 200 and to run the first trained computational model in the vitals module 160 to perform functionality described herein. In aspects, the vitals module 160 can periodically receive an updated trained computational model from the machine learning computer 200, replace the first trained computational model with the updated trained computational model, and run the updated trained computational model in the vitals module 160 to perform functionality described herein.

The inebriation module 170 of the application program 150 of the smart device 100 is configure to determine a pupil-to-iris pixel ratio for an eye of the user in at least one of the plurality of images captured by the smart device 100, and determine a degree of inebriation of the user based on i) the pupil-to-iris pixel ratio and ii) the physiological state for the vital sign, the value for the vital sign, or both the physiological state for the vital sign and the value for the vital sign.

The application program 150 is further configured to generate an inebriation package comprising i) the degree of inebriation and ii) one or more of the pupil-to-iris pixel ratio, the value of the vital sign, and the physiological state; and to send the inebriation package to the central computer 300.

In some aspects, prior to performing an inebriation check as described herein, the application program 150 can be configured to capture a baseline image of the user, such as when the user begins employment with an employer. The application program can run the degree of inebriation on the baseline image and send a baseline inebriation package to the central computer 300 for storage and later comparison with a subsequent inebriation package.

The machine learning computer 200 can include one or more processors, memory, networking cards or interfaces, and other equipment for performing the method and functionality disclosed herein. In embodiments, the machine learning computer 200 can be include multiple computers, located in a brick-and-mortar location, local to the administrator of the machine learning computer 200, in the cloud, or a combination thereof. In FIG. 1, the machine learning computer 200 has a datastore that is configured to store training data. The machine learning computer 200 also has a machine learning (ML) training module 220 that is configured to generate training data sets for training a computational model. The computational model is periodically trained with updated training data sets to generate the updated trained computational model that can be sent by the machine learning computer 200 to the vitals module 160 of the application program 150 running on the smart device 100.

The central computer 300 can include one or more processors, memory, networking cards or interfaces, and other equipment for performing the method and functionality disclosed herein. The central computer 300 is configured to receive an inebriation package comprising the degree of inebriation for the user from the smart device 100, determine if a degree of inebriation exceed a threshold degree (e.g., is elevated or severe), and send an alert or notification to the computer device 400 if the degree of inebriation exceeds the threshold degree. In aspects, determining a threshold degree is exceeded can be performed by analyzing the degree of inebriation in the inebriation package, and determining that an elevated or severe degree exceeds the threshold. In alternative aspects, the threshold is a baseline inebriation package that is compared with the received inebriation package generated at a time after the baseline inebriation package is determined. The central computer 300 can be configured to compare the degree of inebriation in the baseline inebriation package with the degree of inebriation in the subsequent inebriation package, to determine whether the degree of inebriation in the subsequent inebriation package warrants a notification or alert to the employer. For example, if a user has a pupil-to-iris pixel ratio that is often in the elevated range due to circumstances unique to the employee or contractor, then the baseline inebriation package can reflect the elevated range is actually normal for that user, and a subsequent inebriation package containing an elevated degree of inebriation would be compared to the initial inebriation package as being normal for that user, and the central computer 300 would then determine no alert or notification is needed at that time.

In embodiments, the central computer 300 can include multiple computers, located in a brick-and-mortar location, local to the administrator of the central computer 300, in the cloud, or a combination thereof. In embodiments, the central computer 300 can include a distributed computer architecture, such that hardware is geographically distributed to one or more smart devices 100 with the hardware that is geographically closest to the smart device 100. In some aspects, the central computer 300 can include computers embodied as servers that are scalable in the cloud, such as those available from Amazon Web Services.

The computer device 400 can be embodied as a smart phone, tablet, laptop, PC, or other computer device. The computer device 400 can be configured to receive the degree of inebriation from the central computer 300 and to display a notification of the degree of inebriation of the user on the computer device 400. For example, the computer device 400 can be a tablet of a manager or supervisor of various employees and can receive notifications or alerts for users that the central computer 300 has determined to have a degree of inebriation that is greater than a threshold degree of inebriation allowed.

The smart device 100 is networked with the machine learning computer 200 and with the central computer 300.

The smart device 100 and the machine learning computer 200 can be networked via any wired internet connection, wireless internet connection, local area network (LAN), wired intranet connection, wireless intranet connection, or combinations thereof. The networks used for communication between the smart device 100 and the machine learning computer 200 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

The smart device 100 and the central computer 300 can be networked via any wired internet connection, wireless internet connection, local area network (LAN), wired intranet connection, wireless intranet connection, or combinations thereof. The networks used for communication between the smart device 100 and the central computer 300 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

The computer device 400 is networked with the central computer 300. The computer device 400 and the central computer 300 can be networked via any wired internet connection, wireless internet connection, local area network (LAN), wired intranet connection, wireless intranet connection, or combinations thereof. The networks used for communication between the computer device 400 and the central computer 300 can include a Global System for Mobile Communications (GSM), Code-division multiple access (CDMA), General Packet Radio Service (GPRS), Evolution-Data Optimized (EV-DO), Enhanced Data Rates for GSM Evolution (EDGE), Universal Mobile Telecommunications System (UMTS), etc.

Figure 2:
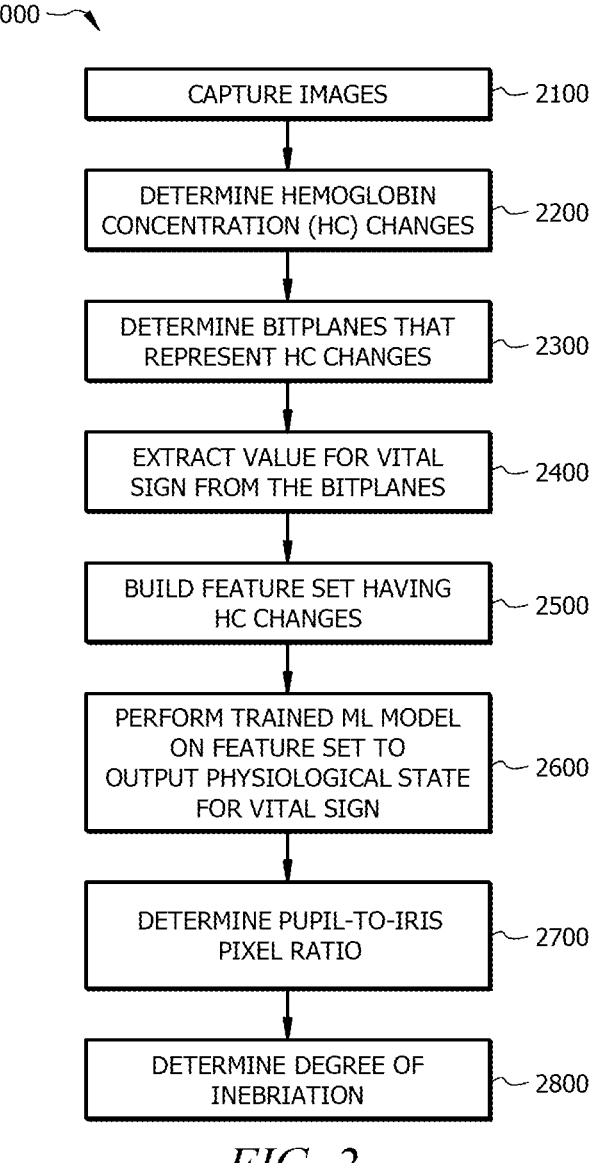
FIG. 2 illustrates a flow diagram of a method for determining one or more vital signs and one or more physiological states associated with the one or more vital signs.

FIG. 2 illustrates a method 2000 for determining one or more vital signs and one or more physiological states associated with the one or more vital signs. The method 2000 is described with reference to components of the computer system 1000 in FIG. 1. The steps of the method 2000 are generally performed by the smart device 100.

In step 2100, the method 2000 includes capturing, by the camera 110 of the smart device 100, a plurality of images of a face of a user. The camera module 120 of the smart device 100 can control the camera 110 to capture the plurality of images. The user of the smart device 100 (e.g., the user) can initiate image capture by instructing the application program 150 to engage with the camera module 120 for image capture (e.g., via a virtual button displayed on the screen of the smart device 100 by the application program 150). The camera module 120 can be configured to cause the camera 110 to capture images at 1, 2, 3, 4, 5, 6, 7, 8, 9, 10, 20, 30, 40, or 50 frames per second, for example. The camera module 120 can be configured to cause the camera 110 to capture images for a period of time, e.g., 5, 10, 15, 20, 25, or 30 seconds; such that changes in hemoglobin concentrations can be determined from the images. The camera module 120 can be configured to construct a file containing a plurality of photo images (e.g., JPEG, PNG formats) or a video file (e.g., MP4, etc.) and send the file to the application program 150. The application program 150 can receive the file from the camera module 120 of the smart device 100.

In step 2200, the method 2000 includes determining, by the smart device 100, a plurality of hemoglobin concentration (HC) changes based on the plurality of images. The images captured by the camera of the smart device can contain the color signature of hemoglobin concentration in the deflected or reflected light. The plurality of HC changes can be determined using the color signatures of the HCs in the images.

In step 2300, the method 2000 includes determining, by the smart device 100, a set of bitplanes of the plurality of images that represent the plurality of hemoglobin concentration (HC) changes of the user. In aspects, the set of bitplanes has a high signal to noise ratio (SNR). In aspects, a set of bitplanes having a high SNR is a set of bitplanes that optimizes or maximizes signal differentiation between different physiological states under the epidermis of the face of the user. In aspects, the vitals module 160 can include a machine learning model to determine the set of bitplanes having a red-green-blue (RGB) pixel bit-combination that maximizes the SNR. An example of a suitable machine learning model can be a K-means clustering model or a Long Short Term Memory (LSTM) neural network model that can obtain an accuracy of signal differentiation and that can determine which bitplane(s) have the highest SNR. The vitals module 160 can be configured to feed the output results of the machine learning model back as input into the machine learning model until two successive machine learning output results have values that are within a tolerance, such as +/−5, 4, 3, 2, or 1%, of one another. In aspects, ML model can be performed on only a portion of the total amount of data (e.g., 70%, 80%, 90% of the bitplanes data), and the vitals module 160 can use the remaining bitplanes data to validate the output of the ML model. In additional aspects, the ML model in step 2300 can be a trained ML model that is trained (e.g., by the machine learning computer 200 or by the application program 150) using a training set of images comprising the plurality of images from a training set of users, EKG data from the training set of users, pneumatic respiration data from the training set of users, blood pressure data from the training set of users, laser Doppler data from the training set of users, oximeter data from the training set of users, or combinations thereof.

In step 2400, the method 2000 includes extracting, by the smart device 100, a value for a vital sign from the bitplanes. An empirically-based HC isolation procedure can be performed on the HC changes, and the set of bitplanes that provides the highest SNR for a vital sign can be determined from the HC changes. The vital sign values can be extracted from the bitplanes. For example, the vital signs of heart rate, respiratory rate, blood pressure, and blood oxygenation index can be extracted by analyzing bitplanes of the plurality of images to determine and isolate a set of the bitplanes that most accurately correlate with EKG, pneumatic respiration, blood pressure, and the blood oxygenation machine data. The extracted vital sign value(s) can be displayed on the smart device 100 (e.g., via the report).

In step 2500, the method 2000 includes building, by the smart device 100, a feature set comprising the plurality of HC changes. In aspects, the feature set can also include stress level ratio(s) for value(s) of the vital sign. For example, one or more digital signal transformations (e.g. Fourier transformations) can be performed on the value of the vital and to obtain a stress level index. By comparing the stress level index against a normative stress index distribution profile that is included with the application program 150, a comparative stress ratio can be determined for the user.

In step 2600, the method 2000 includes performing, by the smart device 100, a trained machine learning (ML) model on the feature set to obtain an output data set comprising a degree of inebriation. In aspects, the trained ML model performed in step 2600 of the method 2000 is not the same model that may optionally be utilized in step 2300 of the method 2000. In aspects, the trained ML model can classify the HC changes as corresponding to a degree of inebriation of the user.

In aspects of this disclosure, the trained ML model that is run on the application program 150 of the smart device 100 is received from the machine learning computer 200. As such, the trained ML model is a computational model that processes a feature set to obtain an output data set. The trained ML model running on the smart device 100 is not continuously updated by the smart device 100. Instead, in these aspects, the machine learning computer 200 continuously or periodically trains the computational model to produce an updated trained ML model (e.g., an updated computational model), and the application program 150 is configured to receive the updated trained ML model from the machine learning computer 200. The updated trained ML model is a later version of the earlier version of the computational model, that can be performed on another feature set to obtain another output data set. The machine learning computer 200 can send or propagate an updated trained ML model to the application program 150 of the smart device 100 periodically, such as daily, weekly, monthly, quarterly, semi-annually, or annually.

In alternative aspects of this disclosure, the smart device 100 can be equipment with chipsets configured for machine learning interference processing on the smart device 100 itself, e.g., an Ethnos model of chipsets commercially available from ARM. In such aspects, the vitals module 160 can use output data sets of the trained ML model to continuously or periodically train the trained ML model running on the vitals module 160 in order to update the trained ML model.

In step 2700, the method 2000 includes determining, by the smart device 100, a pupil-to-iris pixel ratio for an eye of the user in at least one of the plurality of images that is captured by the smart device 100. An example of a technique for determining the pupil-to-iris pixel ratio is described for FIGS. 7A and 7B.

In step 2800, the method 2000 includes determining, by the smart device 100, a degree of inebriation of the user based on i) the pupil-to-iris pixel ratio and ii) the physiological state for the vital sign, the value for the vital sign, or both the physiological state for the vital sign and the value for the vital sign. In aspects, the degree of inebriation can be characterized as normal, elevated, or severe. The degree of inebriation can be included in the inebriation package that is sent from the smart device 100 to the central computer 300.

Figure 3:
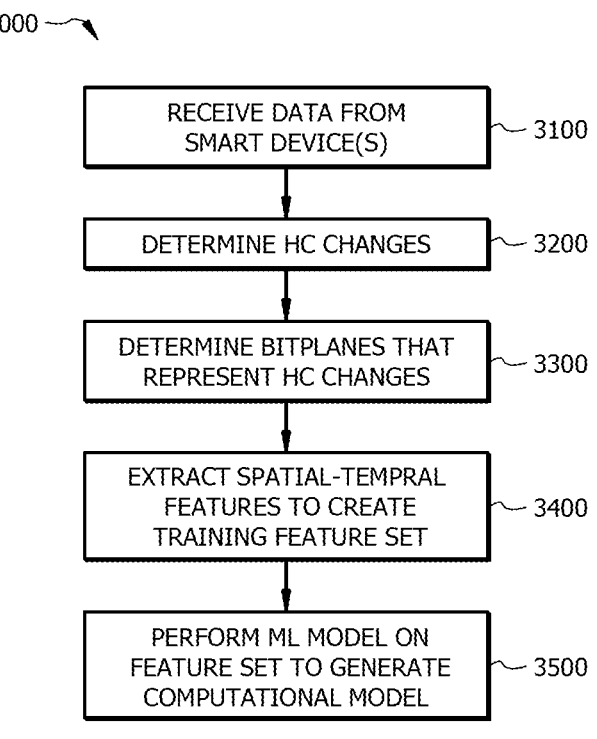
FIG. 3 illustrates a flow diagram of a method for training a machine learning (ML) model that is used as the computational model in the smart device.

FIG. 3 illustrates a flow diagram of a method 3000 for training a machine learning (ML) model that is used as the computational model in the vitals module 160 of the application program 150 running on the smart device 100. The method 3000 is described with reference to the components of the computer system 1000, and particularly with reference to the method 3000 being performed by the ML training module 220 of the machine learning computer 200. Alternative aspects contemplate that the method 3000 can be performed by the vitals module 160 or other module on the application program 150 running on the smart device 100, for example, in aspects where the smart device 100 has a dedicated machine learning interference chipset and memory storage capacity for training data sets.

In step 3100, the method 3000 includes receiving data, by the machine learning computer 200. In aspects, the data can be received from one or more smart devices (e.g., including smart device 100). The data received from any smart device can include any of the data received and generated by the application program 150 and similar application programs on other smart devices. For example, the data received by the machine learning computer 200 can include a file containing a plurality of images from a single scan run on the application program 150 of the smart device 100, several files each containing a plurality of images from several scans run on the application program 150 of the smart device 100, values of HC changes, determined bitplanes for a plurality of images, output results from the machine learning model that is run on the vitals module 160, one or more files containing images, HC changes, output results, or combinations thereof from any number of smart devices that similarly have the application program 150 running thereon.

In additional aspects of step 3100, the data can additionally be received from other data sources. For example, the machine learning computer 200 can receive and store training data from any source. The training data can include images (e.g., files of a sequence of still images or files of video images) of training users that were exposed to stimuli known to elicit specific physiological states (e.g., the International Affective Picture System). Responses may be grouped in a manner that can be reported and communicated as a physiological state of one or a combination of vital signs (e.g., normal, elevated, and severe; or low stress, moderate stress, and high stress; or low pain, moderate pain, and high pain). In aspects, the training data set containing data from users having groups of different skin types. The training data can include images (e.g., files of a sequence of still images or files of video images) of training users that were exposed to stimuli known to elicit specific physiological states (e.g., stimuli from the International Affective Picture System, and/or non-visual stimuli, such as auditory stimuli, taste stimuli, smell stimuli, touch stimuli, or combinations thereof). The training data can additionally include EKG data, pneumatic respiratory data, blood pressure data, and laser Doppler data, and blood oxygenation data of the training users.

The data received by the machine learning computer 200 can be used to build a training data set that is used to build a training feature set for the second machine learning (ML) model in the ML training module 220. In aspects, the training data set contains all data stored at a point in time in the datastore 210 by the machine learning computer 200; alternatively, the training data set contains only all the images stored in the datastore 210. Any data received by the machine learning computer 200 can be stored by the machine learning computer 200 in datastore 210, for access or retrieval when the machine learning computer 200 builds the training data set.

In step 3200, the method 3000 includes determining, by the ML training module 220 of the machine learning computer 200, a plurality of hemoglobin concentration (HC) changes based the images contained in the training data set.

In step 3300, the method 3000 includes determining, by the ML training module 220 of the machine learning computer 200, a set of bitplanes of the images in the training data set that represent the plurality of hemoglobin concentration (HC) changes in the images of the training data set. In aspects, the set of bitplanes has a high signal to noise ratio (SNR). In aspects, a set of bitplanes having a high SNR is a set of bitplanes that optimizes or maximizes signal differentiation between different physiological states under the epidermis of the face(s) that is/are in the images. In aspects, the ML training module 220 can include a first machine learning (ML) model to determine the set of bitplanes having a red-green-blue (RGB) pixel bit-combination that maximizes the SNR. An example of a suitable first ML model that determines bitplanes can be a K-means clustering model or a Long Short Term Memory (LSTM) neural network model that can obtain an accuracy of signal differentiation and that can determine which bitplane(s) have the highest SNR. The ML training module 220 can be configured to feed the output results of the first ML model back as input into the first ML model until two successive machine learning output results have values that are within a tolerance, such as +/−5, 4, 3, 2, or 1%, of one another.

In aspects, the first ML model in the ML training module 220 can be the same ML model that is used in the vitals module 160. However, the first ML model in the ML training module 220 determines bitplanes for HC changes based on images from the training data set (images from many users, training users, etc.), while the ML model on the vitals module 160 determines bitplanes for the HC changes from the plurality of images captured by the smart device 100 for the specific user. Using the same ML model in the ML training module 220 and in the vitals module 160 provides a first layer of data alignment so that the computational model that is trained in the ML training module 220 and sent to the vitals module 160 provides more accurate results for the specific user using the smart device 100.

In step 3400, the method 3000 includes extracting spatial-temporal features from the set of bitplanes that are determined in step 3300, to create a training feature set for the second machine learning (ML) model that is trained om step 3500 to generate the computational model for use in the method 2000. In aspects, a training feature set can be created for each physiological state and a computational model can be generated for each physiological state.

In step 3500, the method 3000 includes performing the second machine learning (ML) model on the training feature set(s) created in step 3400 to generate the computational model that determines a physiological state for an input data set comprising bitplanes described herein. The output of the second ML model is the physiological state for the training feature set. In aspects, the second ML model can be a Long Short Term Memory (LSTM) neural network model or a support vector network model (e.g., utilizing nonlinear classification). In aspects, the second ML model can be performed on only a portion of the total amount of data (e.g., 70%, 80%, 90% of the training feature set), and the ML training module 220 can use the remaining data in the training feature set to validate the output of the second ML model.

In aspects, step 3500 is a training step for the second ML model, and the ML training module 220 can be configured to feed the output results of the second ML model back as input into the second ML model until two successive machine learning output results have values that are within a tolerance, such as +/−5, 4, 3, 2, or 1%, of one another.

After step 3500 is performed (with or with feedback), the second ML model can be used as the computational model that is sent to smart devices (e.g., smart device 100) as an updated version of the model used in the vitals module 160.

It should be noted that the computational model generated in method 3000 provides output for a physiological state of the training feature set that was input to the second ML model. The computational model will not output a physiological state for which it was not trained.

In aspects of the disclosure where the method 3000 is performed by the machine learning computer 200, the machine learning computer 200 can be configured to send or propagate the computational model (also referred to as the second ML model, the updated second ML model, or the updated computational model if method 3000 has already been performed to generate a previous version of the computational model) to the smart device 100 and any other smart device running the application program 150.

In aspects of the disclosure where the method 3000 is performed by the smart device 100, the vitals module 160 of the application program 150 of the smart device 100 can be configured to replace the existing computational model with the updated computational model and run the updated computational model.

Regions of Interest

In aspects of both methods 2000 and 3000, the data can be divided into regions of interest (ROIs) for a face (e.g., eye, nose, cheek, forehead for a face of a user and the training users). For different ROIs, method 3000 can be repeated to generate a computational model to determine the physiological state in each ROI. That is, the method 3000 can be performed for every ROI to generate a computational model for each ROI. It is thus contemplated that multiple computational models (e.g., each corresponding to a particular ROI of a face) can be generated and sent to the application program 150 on the smart device 100. Subsequently, the method 2000 can be performed for each ROI to determine the physiological state in each ROI. It is believed that dividing data into ROIs can increase SNR. The physiological state for each ROI can then be compared or averaged to determine an overall physiological state.

Long Short Term (LSTM) Neural Network Model

For embodiments that utilize a LSTM neural network model, the LSTM neural network model can comprise at least three layers. The first layer is an input layer, which accepts the input data. The second layer is at least one hidden layer, where each hidden layer comprises memory cells. The final layer is an output layer that can generate the output data value based on the hidden layer(s) using a regression technique, such as logistic regression.

Each memory cell in the second layer can include an input gate, a neuron with a self-recurrent connection (a connection to itself), a forget gate, and an output gate. The self-recurrent connection can have a weight (e.g., a weight value of 1.0) so that the state of a memory cell can remain constant from one time step to another. The input gate can permit or prevent an incoming signal to alter the state of the memory cell, the output gate can permit or prevent the state of the memory cell to have an effect on other memory cells, and the forget gate can modulate the self-recurrent connection so that the memory cell remembers or forgets a previous state.

The following equations describe how a layer of memory cells is updated at every time step t, using blood flow as example. In these equations: $\overline{(x)}_t = [x_{1t}, x_{2t}, \ldots, x_{nt}]$ is an input array to the memory cell layer at time t; $W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors. First, compute the values for $i_t$ (the input gate) and $\tilde{C}_t$ (the candidate value for the states of the memory cells at time t): $i_t = \sigma(W_i x_t + U_i h_t - 1 + b_i)$; and $\tilde{C}_t(W_c x_t + U_c h_{t-1} + b_c)$. Second, compute the value for $f_t$ (the activation of the forget gates at time t): $f_t = \sigma(W_f x_t + U_f h_{t-1} + b_f)$. Third, compute $C_t$ (the memory cells' new state at time t): $C_t = i_t * \tilde{C}_t + f_t * C_{t-1}$. Fourth, compute the value of the output gates and the outputs of the output gates: $o_t = \sigma(W_o x_t + U_o h_{t-1} V_o C_t + b_o)$; and $h_t = o_t * \tan h(C_t)$. Based on the model of memory cells, for the blood flow distribution at each time step, we can calculate the output from memory cells. From an input sequence (e.g., $x_0$, $x_1$, $x_2$, . . . ), the memory cells in the hidden layer(s) will produce a representation sequence (e.g., $h_0$, $h_1$, $h_2$ . . . ).

In aspects, the representation sequence can be classified into different conditions. The output layer can generate a probability of each condition based on the representation sequence from the LSTM hidden layer(s). The vector of the probabilities at time step t can be calculated according to the following equation: $p_t = softmax(W_{output} h_t + b_{output})$, where $W_{output}$ is the weight matrix from the hidden layer to the output layer, and $b_{output}$ is the bias vector of the output layer.

The condition with the maximum accumulated probability is the predicted condition of a sequence.

Figure 4:
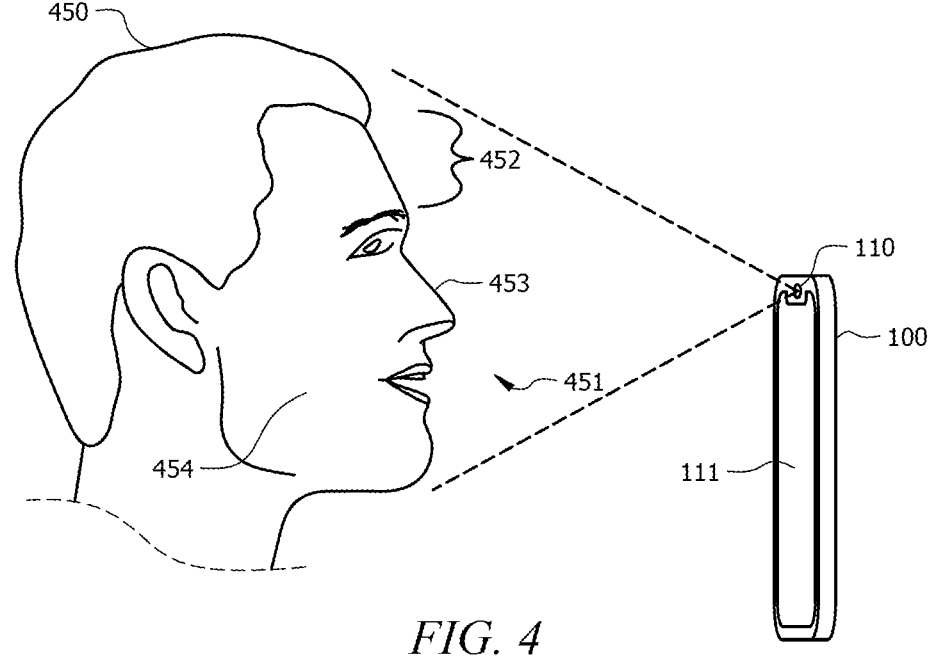
FIG. 4 illustrates a side elevational view of a camera of a smart device capturing a plurality of images of a face of user.

FIG. 4 illustrates a side elevational view of a camera 110 of a smart device 100 capturing a plurality of images of a face 451 of user 450. The regions of interest, e.g., the forehead 452, the nose 453, and the cheek 454 can be seen within the view of the camera 110 of the smart device 100. The smart device 100 is configured to perform the method 2000 of FIG. 2 to display a report of vital sign values and physiological state(s) associated with the vital sign values on the screen 111 of the smart device 100.

Figure 5:
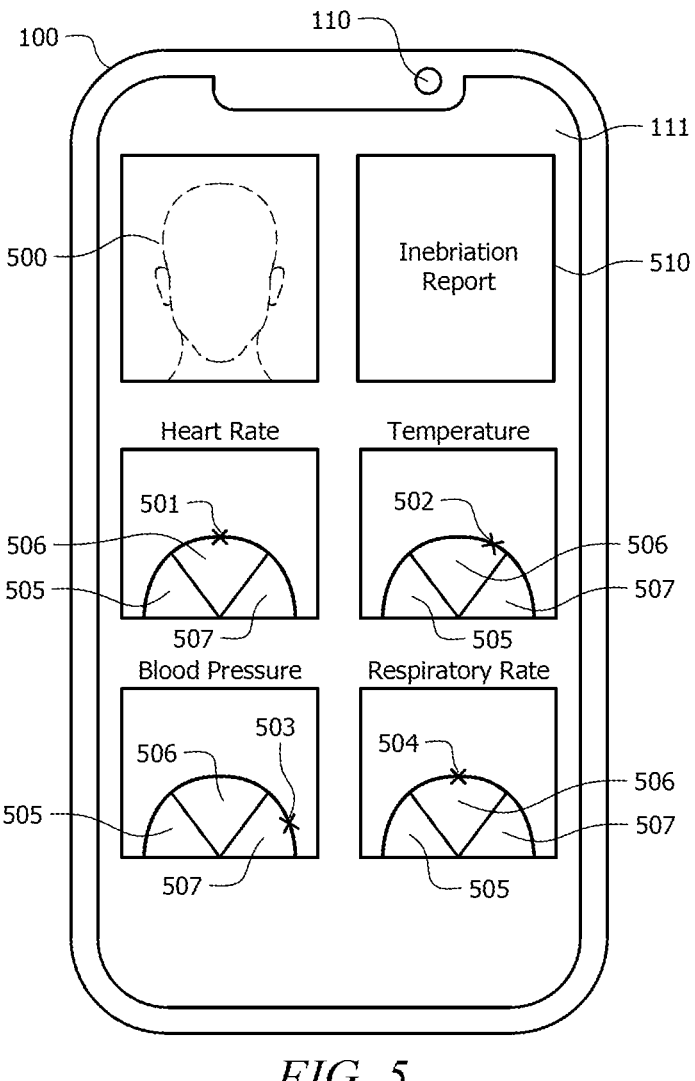
FIG. 5 illustrates a front elevational view of the smart device displaying an exemplary report.

FIG. 5 illustrates a front elevational view of the smart device 100 displaying an exemplary report. The vitals module 160 and the inebriation module 170 of the application program 150 can cause the display module 130 of the smart device 100 to display the report on the screen 111 of the smart device 100. The report can include a photo 500 of the user, an inebriation report 510, and the vital signs illustrated in FIG. 5 are heart rate, temperature, blood pressure, and respiration rate. The vital sign values 501, 502, 503, and 504 correspond to the vital signs of heart rate, temperature, blood pressure, and respiration rate, respectively. The physiological states in FIG. 5 are normal state 505, elevated state 506, and severe state 507. Each vital sign value 501, 502, 503, and 504 is displayed relative to the physiological states of normal state 505, elevated state 506, and severe state 507. That is vital sign value 501 for heart rate is in the elevated state 506. The vital sign value 502 for temperature is in the elevated state 506, close to the border between the elevated state 506 and the severe state 507. The vital sign value 503 for blood pressure is in the severe state 507. The vital sign value 504 for respiratory rate is in the elevated state 506. Examples of inebriation report 510 are in FIGS. 7A and 7B.

Figure 6A:
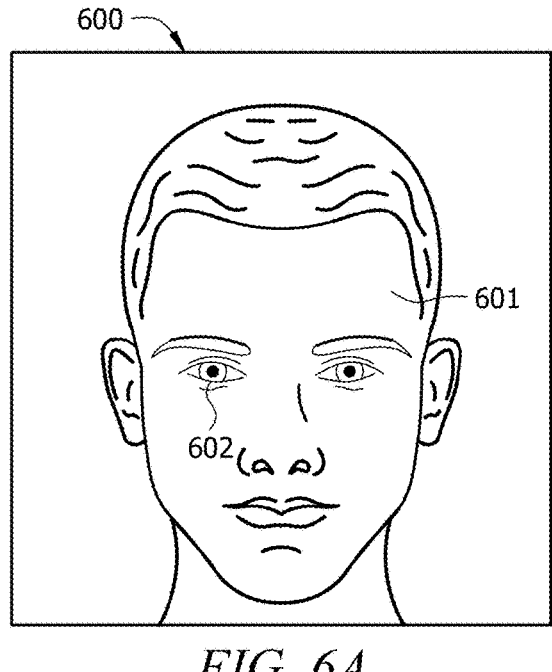
FIGS. 6A and 6B illustrate images of the face of a user of the application.
Figure 6B:
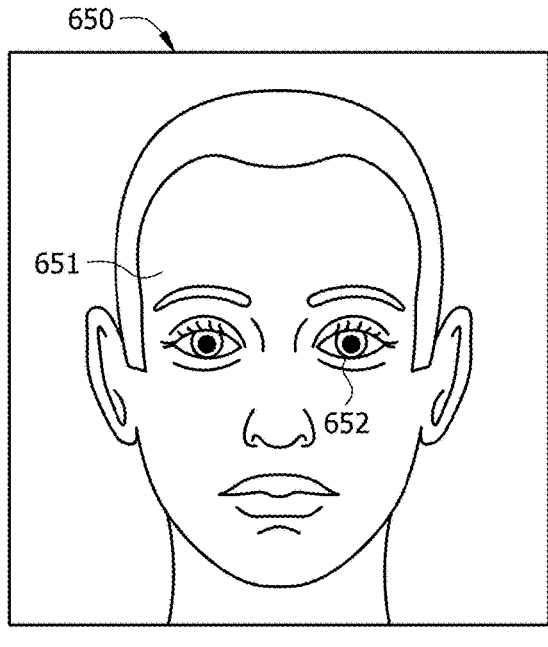

FIGS. 6A and 6B illustrate two-dimensional images of the face of two different users of the application. Each user can have a smart device 100 running the application program 150.

FIG. 6A illustrates a two-dimensional image (e.g., a photo) 600 of the face 601 of a user of the application, and FIG. 6B illustrates another two-dimensional image (e.g., a photo) 650 of the face 651 of another user of the application. The image 600 of the face 601 includes at least one eye 602 (e.g., both eyes of the user in FIG. 6A). The image 650 of the face 651 includes at least one eye 652 (e.g., both eyes of the user in FIG. 6A.

To obtain the image 600, the inebriation module 170 can select the image 600 from the plurality of images captured by the vitals module 160. To obtain the image 650, the inebriation module 170 can select the image 650 from the plurality of images captured by the vitals module 160.

Figure 7A:
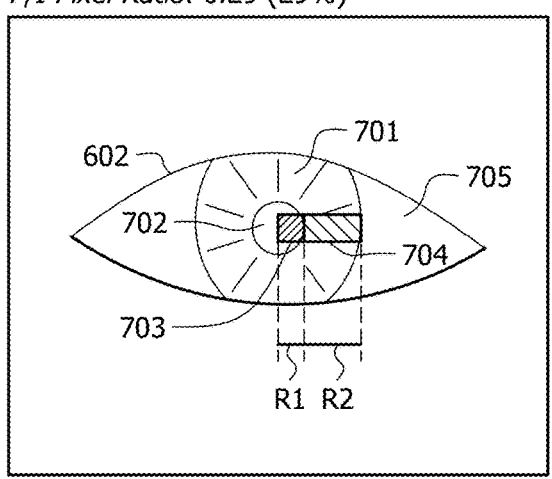
FIGS. 7A and 7B illustrate a report containing the pupil-to-iris ratio and an isolated image of the eye of the user of the application.

FIG. 7A illustrates a report containing the pupil-to-iris ratio and an isolated image of the eye 602 of the user of the application in FIG. 6A. The report in FIG. 7A includes the number of iris pixel, the number of pupil pixels, the pupil-to-iris pixel ratio, an image of the eye 602, bar 703 visually indicating a dimension of the pupil region R1, and bar 704 visually indicating a dimension of the iris region R2.

In aspects, the image 600 is used to determine the pupil-to-pixel ratio. In other aspects, the isolated image of the eye 602 can be used to determine the pupil-to-pixel ratio, and the inebriation module 170 can extract the isolated image of the eye 602 from the image 600 of the face 601 of the user to determine the degree of inebriation and generate the report illustrated in FIG. 7A. The image of the eye 602 in FIG. 7A shows the iris 701 and the pupil 702, as well as the white 705 of the eye 602. Each pixel in the image of FIG. 7A has an RGB (red-green-blue) code. For example, in a simplified scenario, the pixels in the pupil 702 can correspond to a first RGB code, the pixels in the white 705 of the eye 602 can correspond to a second RGB code, and the pixels in the iris 701 can correspond to a third RGB code. The inebriation module 170, using the isolated image of the eye 602, divides the eye 602 into a pupil region R1 of pixels and an iris region R2 of pixels. Then, the inebriation module 170 can determine (e.g., identify, count) the number of pixels having the first RGB code, the number of pixels having the second RGB code, and the number of pixels having the third RGB code. To determine the pupil-to-iris pixel ratio for the eye 602, the inebriation module 170 can divide the number of pixels having the first RGB code by the number of pixels having the third RGB code. In practice, the pupil region R1 may have a first plurality of RGB codes and the iris region R2 may have a second plurality of RGB codes. In such scenarios, the inebriation module 170 is configured to determine/count the number of pixels in the pupil region R1 corresponding to the first plurality of RGB codes, determine/count the number of pixels in the iris region R2 correspond to the second plurality of RGB codes, and divide the number of pixels from the pupil region R1 by the number of pixels from the iris region R2 of the image.

In FIG. 7A, the number of pixel for the iris 701 is 24 pixels, and the number of pixels for the pupil 702 is 7 pixels. Dividing 7 pixels by 24 pixels produces a pupil-to-iris pixel ratio of 0.29 (or 29%).

The inebriation module 170 can then determine a degree of inebriation of the user based on i) the pupil-to-iris pixel ratio and ii) the physiological state for the vital sign, the value for the vital sign, or both the physiological state for the vital sign and the value for the vital sign. With regard to the pupil-to-iris pixel ratio of 0.29 (or 29%) in FIG. 7A, the inebriation module 170 compare the ratio of 0.29 with a threshold ratio. For exemplary purposes, the threshold ratio can be 0.50, where values for the pupil-to-iris ratio less than 0.5 indicate no inebriation, values greater than 0.50 can indicate elevated degree of inebriation, and values greater than 0.75 can indicate severe degree of inebriation. In FIG. 7A, the inebriation module 170 determines that the degree of inebriation is normal because the ratio is 0.29.

The application program 150 then can characterize the degree of inebriation as normal in the inebriation package that is sent to the central computer 300. Alternatively, based on the value of vital signs and physiological state, the application program 150 can characterize the degree of inebriation as normal (in aspects where no vital sign(s) or physiological states exceed any threshold values) or elevated or severe (in aspects where one or more vital sign and one or more physiological state exceed any threshold value).

Figure 7B:
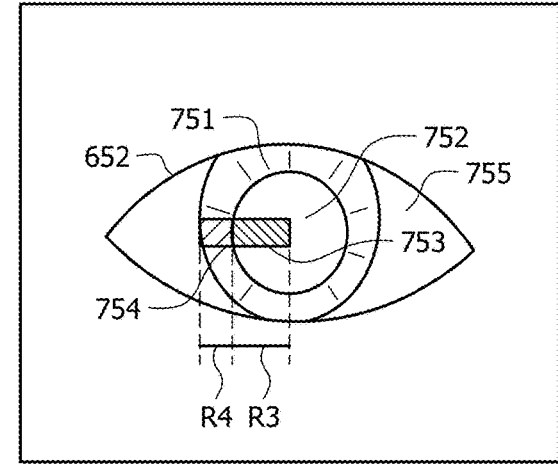

FIG. 7B illustrates a report containing the pupil-to-iris ratio and an isolated image of the eye 652 of the user of the application in FIG. 6B. The report in FIG. 7B includes the number of iris pixels, the number of pupil pixels, the pupil-to-iris pixel ratio, an image of the eye 652, bar 753 visually indicating a dimension of the pupil region R3, and bar 754 visually indicating a dimension of the iris region R4.

In aspects, the image 650 is used to determine the pupil-to-pixel ratio. In other aspects, the isolated image of the eye 652 can be used to determine the pupil-to-pixel ratio, and the inebriation module 170 can extract the isolated image of the eye 652 from the image 650 of the face 651 of the user to determine the degree of inebriation and generate the report illustrated in FIG. 7B. The image of the eye 652 in FIG. 7B shows the iris 751 and the pupil 752, as well as the white 755 of the eye 602. Each pixel in the image of FIG. 7B has an RGB (red-green-blue) code. For example, in a simplified scenario, the pixels in the pupil 752 can correspond to a first RGB code, the pixels in the white 755 of the eye 652 can correspond to a second RGB code, and the pixels in the iris 751 can correspond to a third RGB code. The inebriation module 170, using the isolated image of the eye 652, divides the eye 652 into a pupil region R3 of pixels and an iris region R4 of pixels. Then, the inebriation module 170 can determine (e.g., identify, count) the number of pixels having the first RGB code, the number of pixels having the second RGB code, and the number of pixels having the third RGB code. To determine the pupil-to-iris pixel ratio for the eye 652, the inebriation module 170 can divide the number of pixels having the first RGB code by the number of pixels having the third RGB code. In practice, the pupil region R3 may have a first plurality of RGB codes and the iris region R4 may have a second plurality of RGB codes. In such scenarios, the inebriation module 170 is configured to determine/count the number of pixels in the pupil region R3 corresponding to the first plurality of RGB codes, determine/count the number of pixels in the iris region R4 correspond to the second plurality of RGB codes, and divide the number of pixels from the pupil region R3 by the number of pixels from the iris region R4 of the image.

In FIG. 7B, the number of pixel for the iris 751 is 194 pixels, and the number of pixels for the pupil 752 is 144 pixels. Dividing 144 pixels by 194 pixels produces a pupil-to-iris pixel ratio of 0.74 (or 74%).

The inebriation module 170 can then determine a degree of inebriation of the user based on i) the pupil-to-iris pixel ratio and ii) the physiological state for the vital sign, the value for the vital sign, or both the physiological state for the vital sign and the value for the vital sign. With regard to the pupil-to-iris pixel ratio of 0.74 (or 74%) in FIG. 7B, the inebriation module 170 compare the ratio of 0.74 with a threshold ratio. For exemplary purposes, the threshold ratio can be 0.50, where values for the pupil-to-iris ratio less than 0.50 indicate no inebriation, values greater than 0.50 can indicate elevated degree of inebriation, and values greater than 0.75 can indicate severe degree of inebriation. In FIG. 7B, the inebriation module 170 determines that the degree of inebriation is elevated because the ratio is 0.74. The application program 150 then can characterize the degree of inebriation as elevated in the inebriation package that is sent to the central computer 300. Alternatively, based on the value of vital signs and physiological state, the application program 150 can characterize the degree of inebriation as elevated (in aspects where no vital sign(s) or physiological states exceed any threshold values) or severe (in aspects where one or more vital sign and one or more physiological state exceed any threshold value).

Additional Disclosure

Accordingly, the scope of protection is not limited by the description set out above but is only limited by the claims which follow, that scope including all equivalents of the subject matter of the claims. Each and every claim is incorporated into the specification as part of the disclosure. Thus, the claims are a further description and are an addition to the detailed description. The disclosures of all patents, patent applications, and publications cited herein are hereby incorporated by reference.

Clause 1. A method comprising: capturing, by a camera of a smart device, a plurality of images of a face of a user; determining, by the smart device, a plurality of hemoglobin concentration (HC) changes based on the plurality of images; determining, by the smart device, a set of bitplanes of the plurality of images that represent the plurality of hemoglobin concentration (HC) changes of the user; extracting, by the smart device, a value for a vital sign from the plurality of HC changes; building, by the smart device, a feature set comprising the plurality of HC changes; performing, by the smart device, a trained machine learning model comprising a computational model on the feature set to obtain an output data set comprising a physiological state for the vital sign; determining, by the smart device, a pupil-to-iris pixel ratio for an eye of the user in at least one of the plurality of images; and determining, by the smart device, a degree of inebriation of the user based on i) the pupil-to-iris pixel ratio and ii) the physiological state for the vital sign, the value for the vital sign, or both the physiological state for the vital sign and the value for the vital sign.

Clause 2. The method of clause 1, wherein determining the pupil-to-iris pixel ratio comprises: determining, by the smart device, a first number of pixels that corresponds to a pupil of the eye of the user in the at least one of the plurality of images; determining, by the smart device, a second number of pixels that corresponds to an iris of an eye of the user in the at least one of the plurality of images; and dividing, by the smart device, the first number by the second number to obtain the pupil-to-iris pixel ratio.

Clause 3. The method of clause 1 or 2, further comprising: receiving, by the smart device from a machine learning computer, the trained machine learning model.

Clause 4. The method of any one of clauses 1 to 3, further comprising: receiving, by the smart device from the machine learning computer, a second trained machine learning model; and performing, by the smart device, the second trained machine learning model on additional feature sets to obtain additional output data sets comprising physiological states.

Clause 5. The method of any one of clauses 1 to 4, further comprising: generating, by the smart device, an inebriation package containing i) the degree of inebriation and optionally ii) a value for the vital sign and the physiological state; and sending the inebriation package to a central computer.

Clause 6. The method of clause 5, wherein the central computer compares the inebriation package with a baseline package to determine to send a notification or alert to an employer computer device.

Clause 7. The method of clause 5 or 6, wherein the degree of inebriation in the inebriation package is characterized normal, elevated, or severe.

Clause 8. The method of any one of clauses 1 to 7, wherein the machine learning model is a K-means clustering model or a neural network model.

Clause 9. The method of any one of clauses 1 to 8, further comprising: receiving, by a machine learning computer from the smart device, the plurality of images; determining, by a ML training module of the machine learning computer, a second plurality of hemoglobin concentration (HC) changes based on the plurality of images; determining, by the ML training module of the machine learning computer, a second set of bitplanes of the plurality of images that represent the second plurality of hemoglobin concentration (HC) changes; extracting, by the ML training module of the machine learning computer, spatial-temporal features from the second set of bitplanes; creating, by the ML training module of the machine learning computer, a training feature set; and performing, by the ML training module of the machine learning computer, a second machine learning model on the training feature set to generate the computational model.

Clause 10. The method of clause 9, wherein an output of the second machine learning model is the physiological state.

Clause 11. A computer system comprising a smart device, wherein the smart device is configured to: capture, by camera of the smart device, a plurality of images of a face of a user; determine, by an application program running on the smart device, a plurality of hemoglobin concentration (HC) changes based on the plurality of images; determine, by the application program, a set of bitplanes of the plurality of images that represent the plurality of hemoglobin concentration (HC) changes of the user; extract, by the application program, a value for a vital sign from the plurality of HC changes; build, by the application program, a feature set comprising the plurality of HC changes; perform, by the application program, a trained machine learning model comprising a computational model on the feature set to obtain an output data set comprising a physiological state for the vital sign; determine, by the application program, a pupil-to-iris pixel ratio for an eye of the user in at least one of the plurality of images; and determine, by the application program, a degree of inebriation of the user based on i) the pupil-to-iris pixel ratio and ii) the physiological state for the vital sign, the value for the vital sign, or both the physiological state for the vital sign and the value for the vital sign.

Clause 12. The computer system of clause 11, wherein determining the pupil-to-iris pixel ratio comprises: determining, by the application program, a first number of pixels that corresponds to a pupil of the eye of the user in the at least one of the plurality of images; determining, by the application, a second number of pixels that corresponds to an iris of an eye of the user in the at least one of the plurality of images; and dividing, by the application program, the first number by the second number to obtain the pupil-to-iris pixel ratio.

Clause 13. The computer system of clause 11 or 12, wherein the application program of the smart device is further configured to: receive, from a machine learning computer, the trained machine learning model.

Clause 14. The computer system of clause 13, wherein the application program of the smart device is further configured to: receive, from the machine learning computer, a second trained machine learning model; and perform the second trained machine learning model on additional feature sets to obtain additional output data sets comprising physiological states.

Clause 15. The computer system of any one of clauses 11 to 14, wherein the application program of the smart device is further configured to: generate an inebriation package containing i) the degree of inebriation and optionally ii) a value for the vital sign and the physiological state; and send the inebriation package to a central computer.

Clause 16. The computer system of clause 15, wherein the central computer is configured to compares the inebriation package with a baseline package to determine to send a notification or alert to an employer computer device.

Clause 17. The computer system of clause 15 or 16, wherein the degree of inebriation in the inebriation package is characterized normal, elevated, or severe.

Clause 18. The computer system of any one of clauses 11 to 17, wherein the machine learning model is a K-means clustering model or a neural network model.

Clause 19. The computer system of any one of clauses 11 to 18, further comprising a machine learning computer, wherein the machine learning computer is configured to: receive, from the smart device, the plurality of images;

determine, by a ML training module of the machine learning computer, a second plurality of hemoglobin concentration (HC) changes based on the plurality of images; determine, by the ML training module of the machine learning computer, a second set of bitplanes of the plurality of images that represent the second plurality of hemoglobin concentration (HC) changes; extract, by the ML training module of the machine learning computer, spatial-temporal features from the second set of bitplanes; create, by the ML training module of the machine learning computer, a training feature set based on the spatial-temporal features; and perform, by the ML training module of the machine learning computer, a second machine learning model on the training feature set to generate the computational model.

Clause 20. The computer system of clause 19, wherein an output of the second machine learning model is the physiological state.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A method comprising:
capturing, by a camera of a smart device, a plurality of images of a face of a user;
determining, by the smart device, a plurality of hemoglobin concentration (HC) changes based on the plurality of images;
determining, by the smart device, a set of bitplanes of the plurality of images that represent the plurality of hemoglobin concentration (HC) changes of the user;
extracting, by the smart device, a value for a vital sign from the plurality of HC changes or from the set of bitplanes;
building, by the smart device, a feature set comprising the plurality of HC changes;
performing, by the smart device, a trained machine learning model comprising a computational model on the feature set to obtain an output data set comprising a physiological state for the vital sign;
determining, by the smart device, a pupil-to-iris pixel ratio for an eye of the user in at least one of the plurality of images; and
determining, by the smart device, a degree of inebriation of the user based on i) the pupil-to-iris pixel ratio and ii) the physiological state for the vital sign, the value for the vital sign, or both the physiological state for the vital sign and the value for the vital sign.

2. The method of claim 1, wherein determining the pupil-to-iris pixel ratio comprises:

determining, by the smart device, a first number of pixels that corresponds to a first red-green-blue (RGB) code for a pupil of the eye of the user in the at least one of the plurality of images;
determining, by the smart device, a second number of pixels that corresponds to a second red-green-blue (RGB) code for an iris of an eye of the user in the at least one of the plurality of images; and
dividing, by the smart device, the first number by the second number to obtain the pupil-to-iris pixel ratio.

3. The method of claim 1, further comprising:
receiving, by the smart device from a machine learning computer, the trained machine learning model.

4. The method of claim 3, further comprising:
receiving, by the smart device from the machine learning computer, a second trained machine learning model; and
performing, by the smart device, the second trained machine learning model on additional feature sets to obtain additional output data sets comprising physiological states.

5. The method of claim 1, further comprising:
generating, by the smart device, an inebriation package containing i) the degree of inebriation and optionally ii) a value for the vital sign and the physiological state; and
sending the inebriation package to a central computer.

6. The method of claim 5, wherein the central computer compares the inebriation package with a baseline package to determine to send a notification or alert to an employer computer device, wherein the degree of inebriation in the inebriation package is characterized normal, elevated, or severe.

7. The method of claim 1, wherein the vital sign comprises a heart rate, a respiratory rate, a blood pressure, a blood oxygen index, or combinations thereof.

8. The method of claim 1, wherein the trained machine learning model is a K-means clustering model or a neural network model.

9. The method of claim 1, further comprising:
receiving, by a machine learning computer from the smart device, the plurality of images;
determining, by a ML training module of the machine learning computer, a second plurality of hemoglobin concentration (HC) changes based on the plurality of images;
determining, by the ML training module of the machine learning computer, a second set of bitplanes of the plurality of images that represent the second plurality of hemoglobin concentration (HC) changes;
extracting, by the ML training module of the machine learning computer, spatial-temporal features from the second set of bitplanes;
creating, by the ML training module of the machine learning computer, a training feature set; and
performing, by the ML training module of the machine learning computer, a second machine learning model on the training feature set to generate the computational model.

10. The method of claim 9, wherein an output of the second machine learning model is the physiological state.

11. A computer system comprising a smart device, wherein the smart device is configured to:
capture, by camera of the smart device, a plurality of images of a face of a user;

determine, by an application program running on the smart device, a plurality of hemoglobin concentration (HC) changes based on the plurality of images;

determine, by the application program, a set of bitplanes of the plurality of images that represent the plurality of hemoglobin concentration (HC) changes of the user;

extract, by the application program, a value for a vital sign from the plurality of HC changes or from the set of bitplanes;

build, by the application program, a feature set comprising the plurality of HC changes;

perform, by the application program, a trained machine learning model comprising a computational model on the feature set to obtain an output data set comprising a physiological state for the vital sign;

determine, by the application program, a pupil-to-iris pixel ratio for an eye of the user in at least one of the plurality of images; and determine, by the application program, a degree of inebriation of the user based on i) the pupil-to-iris pixel ratio and ii) the physiological state for the vital sign, the value for the vital sign, or both the physiological state for the vital sign and the value for the vital sign.

12. The computer system of claim 11, wherein determining the pupil-to-iris pixel ratio comprises:

determining, by the application program, a first number of pixels that corresponds to a first red-green-blue (RGB) code for a pupil of the eye of the user in the at least one of the plurality of images;

determining, by the application program, a second number of pixels that corresponds to a second red-green-blue (RGB) code for an iris of an eye of the user in the at least one of the plurality of images; and dividing, by the application program, the first number by the second number to obtain the pupil-to-iris pixel ratio.

13. The computer system of claim 11, wherein the application program of the smart device is further configured to:

receive, from a machine learning computer, the trained machine learning model.

14. The computer system of claim 13, wherein the application program of the smart device is further configured to:

receive, from the machine learning computer, a second trained machine learning model; and perform the second trained machine learning model on additional feature sets to obtain additional output data sets comprising physiological states.

15. The computer system of claim 11, wherein the application program of the smart device is further configured to:

generate an inebriation package containing i) the degree of inebriation and optionally ii) a value for the vital sign and the physiological state; and send the inebriation package to a central computer.

16. The computer system of claim 15, wherein the central computer is configured to compares the inebriation package with a baseline package to determine to send a notification or alert to an employer computer device, wherein the degree of inebriation in the inebriation package is characterized normal, elevated, or severe.

17. The computer system of claim 15, wherein the vital sign comprises a heart rate, a respiratory rate, ab od pressure, a blood oxygen index, or combinations thereof.

18. The computer system of claim 11, wherein the trained machine learning model is a K-means clustering model or a neural network model.

19. The computer system of claim 11, further comprising a machine learning computer, wherein the machine learning computer is configured to:

receive, from the smart device, the plurality of images;

determine, by a ML training module of the machine learning computer, a second plurality of hemoglobin concentration (HC) changes based on the plurality of images;

determine, by the ML training module of the machine learning computer, a second set of bitplanes of the plurality of images that represent the second plurality of hemoglobin concentration (HC) changes;

extract, by the ML training module of the machine learning computer, spatial-temporal features from the second set of bitplanes;

create, by the ML training module of the machine learning computer, a training feature set based on the spatial-temporal features; and perform, by the ML training module of the machine learning computer, a second machine learning model on the training feature set to generate the computational model.

20. The computer system of claim 19, wherein an output of the second machine learning model is the physiological state.

* * * * *